United States Patent
Sale et al.

(10) Patent No.: US 6,772,635 B1
(45) Date of Patent: Aug. 10, 2004

(54) METHOD AND APPARATUS FOR REMOTE DELIVERY AND MANIPULATION OF A MINIATURE TOOL ADJACENT A WORK PIECE IN A RESTRICTED SPACE

(75) Inventors: Christopher H. Sale, Murrysville, PA (US); Daniel R. Kaltenbaugh, Bakerstown, PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 169 days.

(21) Appl. No.: 10/090,808

(22) Filed: Mar. 6, 2002

(51) Int. Cl.[7] .............................................. G01N 29/04
(52) U.S. Cl. .......................................... 73/622; 73/633
(58) Field of Search ........................ 73/622, 634, 637, 73/638, 597–600, 629, 618, 624–625, 627–628, 623, 633

(56) References Cited

U.S. PATENT DOCUMENTS 4,217,782 A * 8/1980 Pont ............................. 73/637
4,586,379 A * 5/1986 Burkhardt, Jr. .............. 73/622

* cited by examiner

Primary Examiner—Hezron Williams
Assistant Examiner—Rose M. Miller
(74) Attorney, Agent, or Firm—Richard A. Morgan; Paul A. Gottlieb

(57) ABSTRACT

An apparatus for remote delivery and manipulation of a miniature tool adjacent a work piece in a restricted space, includes a tool carrier, a carriage for manipulating the tool carrier relative to the work piece, a first actuator for operating the carriage, and an optional remote secondary operating actuator for operating the first actuator.

18 Claims, 8 Drawing Sheets

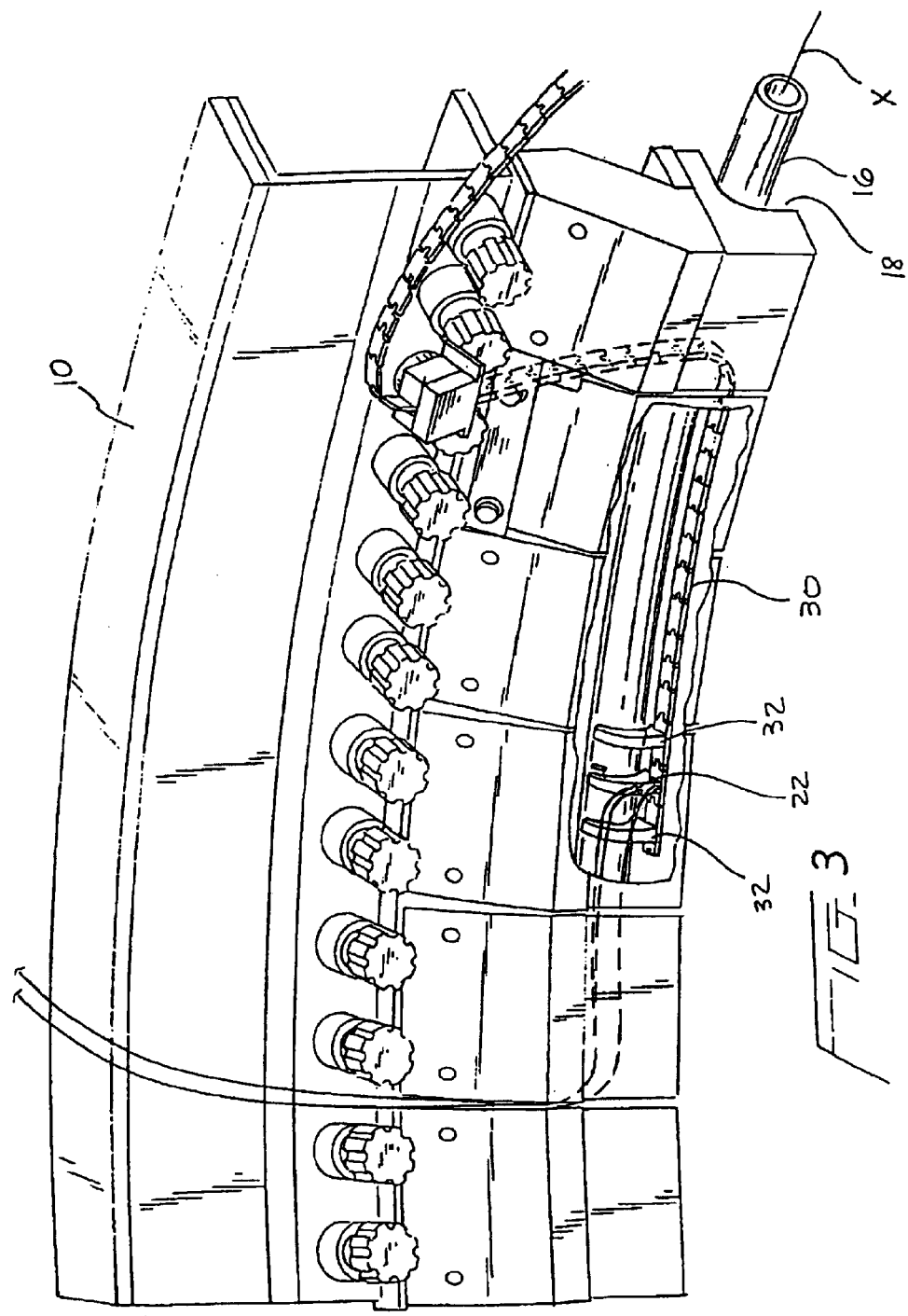

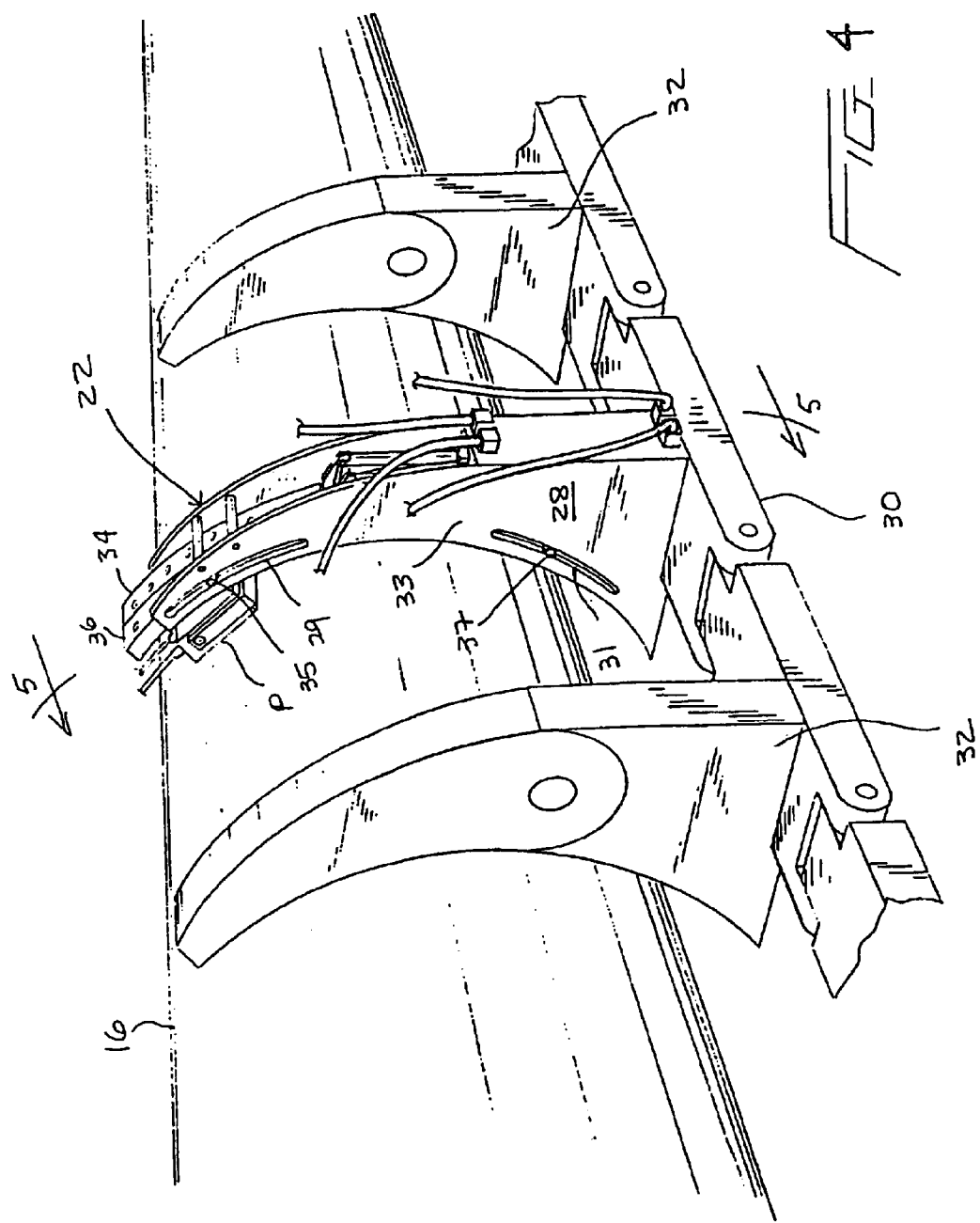

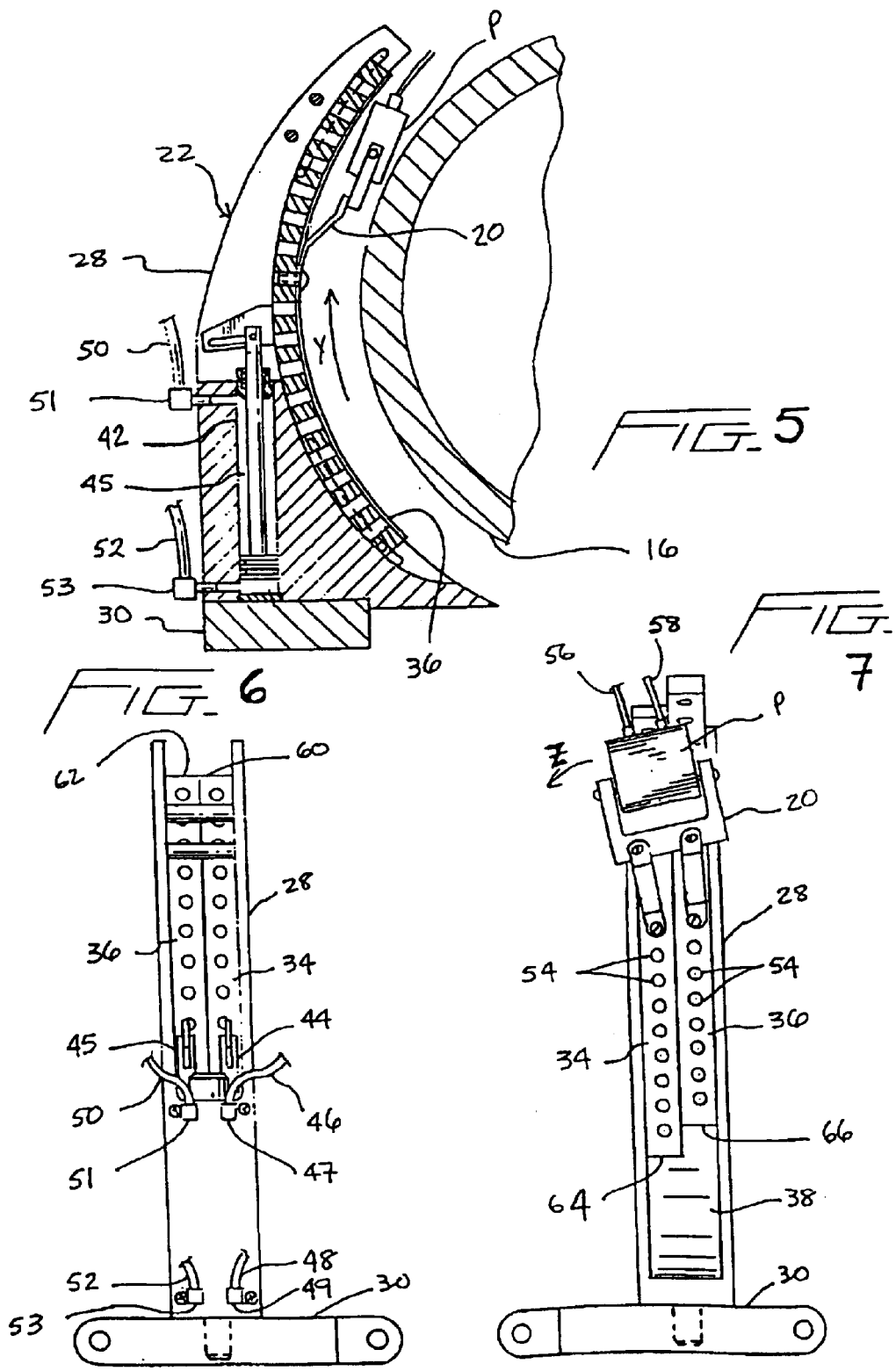

METHOD AND APPARATUS FOR REMOTE DELIVERY AND MANIPULATION OF A MINIATURE TOOL ADJACENT A WORK PIECE IN A RESTRICTED SPACE

FIELD AND HISTORICAL BACKGROUND OF THE INVENTION

This invention was made with Government support under a contract awarded by the U.S. Department of Energy. The Government has certain rights in the invention.

The present invention is directed to an apparatus for remote delivery and manipulation of a miniature tool, and more particularly to a hydraulically operated manipulator system for remote delivery and manipulation of a tool, such as an ultrasonic test sizing probe, adjacent a work piece that can be either submerged in a fluid or in a dry environment in a restricted space.

Presently, there is no system or technology available that could facilitate the sizing of ultrasonic test (UT) indications in this design of a nuclear reactor vessel closure seal without the removal of the closure mechanism. The vessel closure mechanisms secure a head (lid) onto a reactor vessel. Removal of the closure mechanisms is very costly and time consuming, and is likely to result in their destruction. Access to the closure seal is very restricted with the closure mechanisms in place, and manual sizing of the indications (defects, such as cracks, flaws, etc) is almost impossible. The only accessibility to the closure seal, with the closure mechanisms in place, is through small trapezoidal openings between each closure mechanism.

FIG. 1 illustrates the seal area of a typical reactor vessel. As shown in FIGS. 1 and 3, closure blocks 10 are circumferentially arranged between the top of the reactor pot 12 and the inside of a lid 14. A closure seal 16 is positioned underneath the closure blocks 10 in the small opening 18 below the closure blocks 10. As can be seen, the installed closure mechanisms both limit the size of the delivery and manipulator system that can be inserted between them, and limit the size of a manipulating device in the area surrounding the closure seal. Another constraint is the location of the closure seal from the closest work space. The closure seal is typically situated about three feet below the closest space where ultrasonic test personnel can position themselves, and some locations are obstructed by piping or cables.

Therefore, there is a need for an apparatus for remote delivery and manipulation of miniaturized tools in a restricted area, such as an ultrasonic test sizing probe to characterize and size ultrasonic test indications in a reactor vessel closure seal that would otherwise be inaccessible without the removal of the closure mechanisms.

OBJECTS AND SUMMARY OF THE INVENTION

The principal object of the present invention is to provide an apparatus for remote delivery and manipulation of a miniature tool adjacent to a work piece that can be either submerged in a fluid or in a dry environment, in a restricted space.

An object of the present invention is to provide an apparatus for remote delivery and manipulation of a miniature tool with precision in multiple environments with limited access in a repeatable, controlled manner.

Another object of the present invention is to provide an apparatus for remote delivery and manipulation of a miniature probe to characterize and size ultrasonic test indications in a vessel closure seal in a restricted space.

Still yet another object of the present invention is to provide an apparatus for remote delivery and manipulation of a miniature tool, such as a probe, which is capable of characterizing and sizing ultrasonic test indications in the closure seal of a reactor vessel without the removal of the closure mechanisms.

An additional object of the present invention is to provide an apparatus for remote delivery and manipulation of a miniature tool which is capable of moving the tool in two dimensions (along X and Y axes) over the surface being scanned, as well as skewing the tool (rotate about the Z axis).

Yet an additional object of the present invention is to provide an apparatus for remote delivery and manipulation of a miniature tool which provides sufficient manipulation of the ultrasonic test sizing probe to utilize the tip diffraction ultrasonic testing sling technique.

A further object of the present invention is to provide an apparatus for remote delivery and manipulation of a miniature tool which can be used for ultrasonic test inspections, video probe inspections, shadow probe inspections, and eddy current inspections.

Yet a further object of the present invention is to provide an apparatus for remote delivery and manipulation of a miniature tool which could be used for remote cutting and grinding operations.

In summary, the main object of the present invention is to provide an apparatus for remote delivery and manipulation of a miniature tool, such as an ultrasonic test sizing probe, to perform various operations in a restricted space and under several environmental conditions without having to first remove or dismantle associated mechanisms and components around a work piece. In particular, the apparatus of the present invention can be used to deliver and manipulate a miniaturized ultrasonic test sizing probe to characterize and size ultrasonic test indications in a reactor vessel closure seal that would otherwise be inaccessible without the removal of the closure mechanisms.

In accordance with the present invention, an apparatus for remote delivery and manipulation of a miniature tool adjacent a work piece in a restricted space, includes a tool carrier, a carriage assembly for manipulating the tool carrier relative to the work piece, and a remote hydraulic actuator for operating the carriage assembly.

BRIEF DESCRIPTION OF THE DRAWINGS

The above and other objects, novel features and advantages of the present invention will become apparent from the following detailed description of the invention, as illustrated in the accompany drawings, in which:

FIG. 3 is a view showing the apparatus of the invention being delivered to the space between the closure seal and closure blocks;

FIG. 4 is an enlarged view of the apparatus of the invention shown adjacent the closure seal;

FIG. 5 is a sectional view of the carriage assembly taking along the lines 5—5 of FIG. 4;

FIG. 6 is a rear elevational view of the carriage assembly;

FIG. 7 is a front elevational view of the carriage assembly;

DETAILED DESCRIPTION OF THE INVENTION

Figure 1:
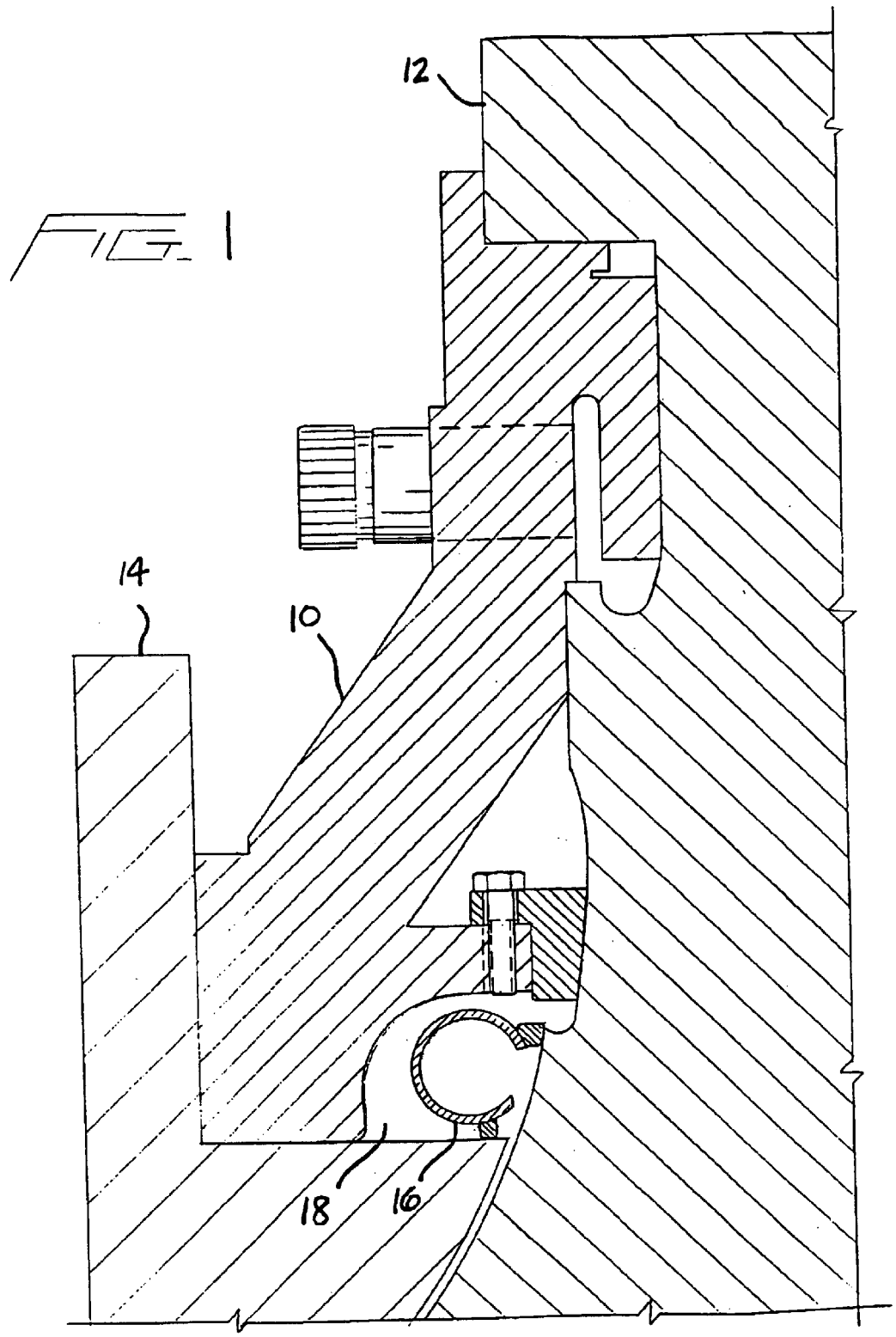
FIG. 1 is a sectional elevational view of a closure seal area between a nuclear reactor pot and the associated lid.
Figure 2:
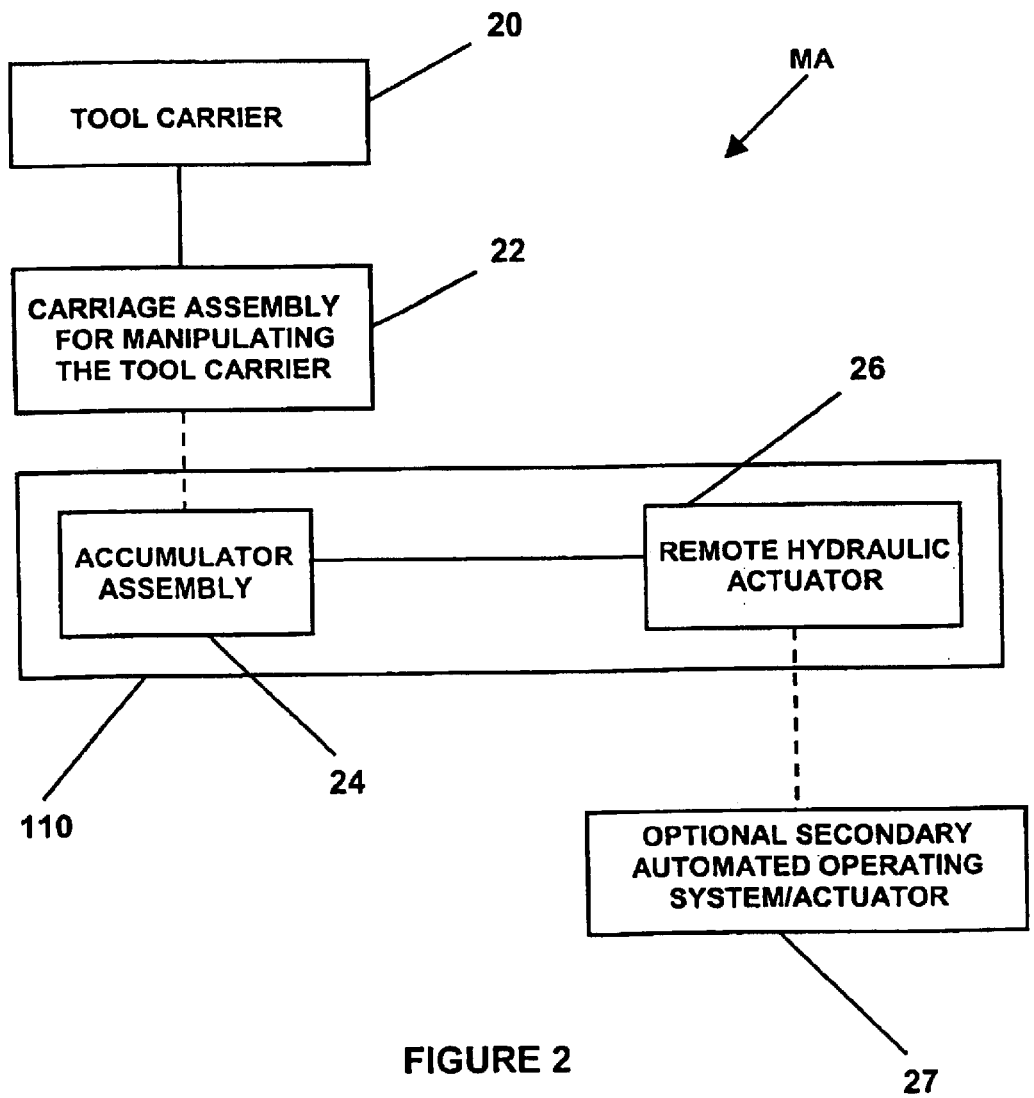
FIG. 2 is a block diagram showing the various components of the apparatus of the present invention.
Figure 2A:
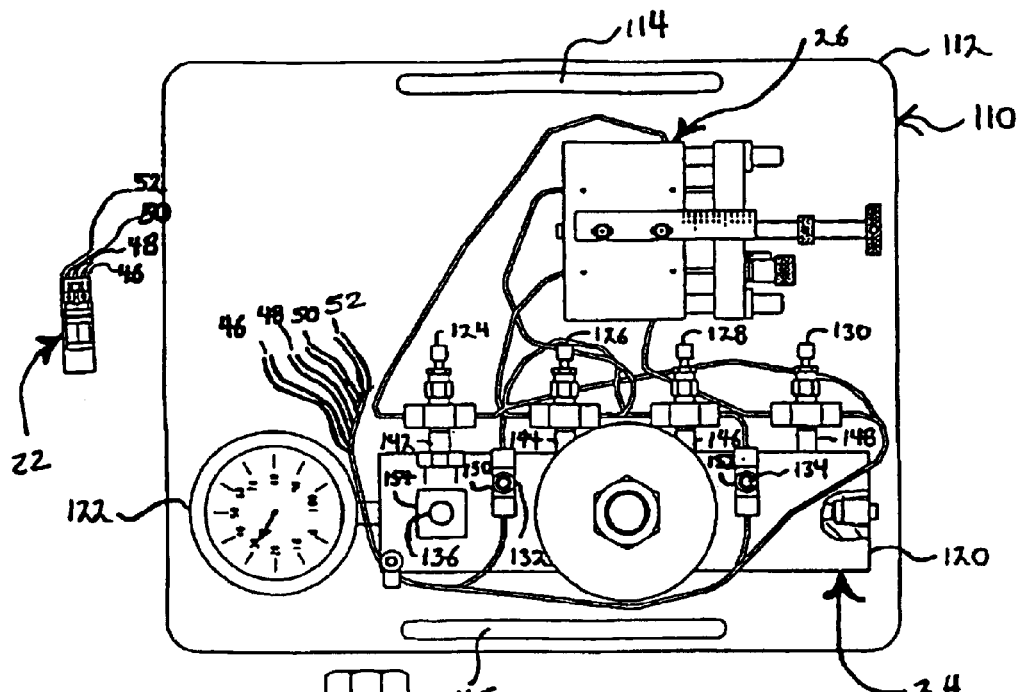
FIG. 2a is a top view showing the various components of the remote operating system.
Figure 2B:
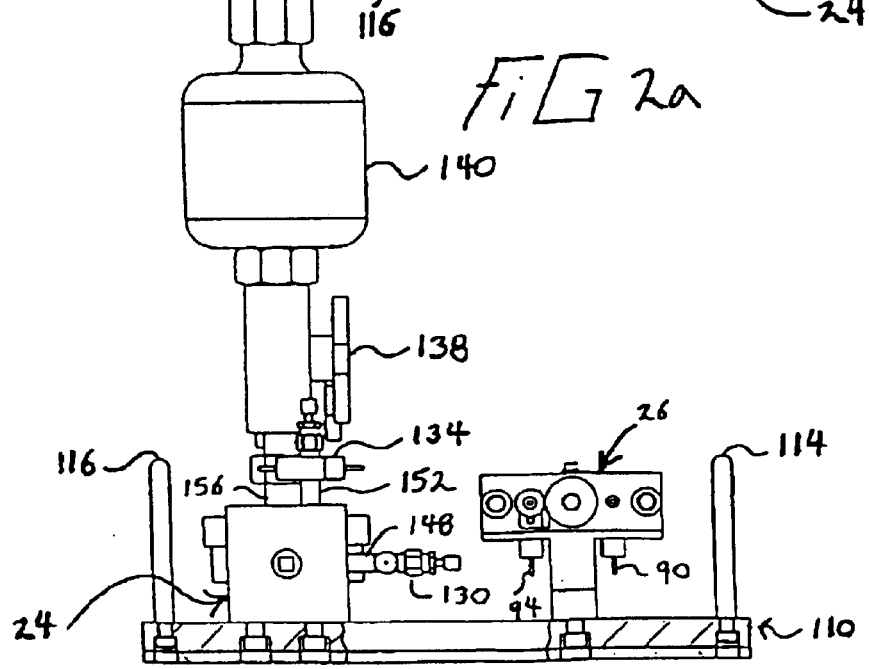
FIG. 2b is a side view showing the various components of the remote operating system.

As best shown in FIGS. 2, 2a, and 2b, the manipulator apparatus MA of the invention includes a tool carrier 20, a carriage assembly 22, and a remote operating system 110. The remote system 110 includes an accumulator assembly 24 and a remote hydraulic actuator assembly 26. It is noted that although the current system has a single remote actuator 26, an optional secondary operating system/actuator 27 may be incorporated into the system to automate/operate the remote hydraulic actuator 26. The secondary operating system/actuator 27 may be connected to the remote actuator 26 (either hydraulically, mechanically, electrically, etc.) and automated through any combination of electrical motors, encoders, computers, imaging software, etc. The accumulator assembly 24 and the hydraulic actuator 26 operate the carriage assembly 22 and are positioned at a remote location for operation by appropriate personnel.

As best shown in FIGS. 4–7, the carriage assembly 22 includes a generally arcuate frame 28 mounted on a delivery chain 30. Preferably, the carriage assembly 22 is laterally spaced from and is positioned between two stabilizers 32 that have similar arcuate configuration. The delivery chain 30 is part of a conventional lance delivery system used in the present invention to deliver a probe P adjacent the vessel closure seal 16 for inspection purposes. (It is noted that other compatible delivery systems, such as track or cable systems, may also be used.) The stabilizers 32 are provided to maintain a sufficient distance from the closure seal 16. As best shown in FIG. 3, the delivery chain 30 moves the carriage assembly 22 axially along the longitudinal axis x of the closure seal.

As best shown in FIGS. 6–7, the arcuate frame 28 of the carriage assembly 22 accommodates two laterally disposed tracks 34 and 36 that slide along an arcuate recess 38 therein. Each track 34 and 36 is operated by individual hydraulic cylinders 40 (not shown; next to, and identical to 42) and 42, respectively. Each cylinder 40 and 42 includes a double acting piston 44 and 45, respectively, for causing the tracks 34 and 36 to independently move in a circumferential direction in the recess 38 (see arrow Y in FIG. 5). As best shown in FIG. 4, the frame 28 is provided with upper and lower arcuate slots 29 and 31 in the side wall 33 thereof for receiving corresponding cams 35 and 37 mounted on track member 36. (It is noted that the side wall opposite to the wall 33 would have similar slots to receive cams from the track member 34.)

In FIG. 6, reference numerals 46 and 48 indicate hydraulic lines for the cylinder 40, and reference numerals 50 and 52 indicate hydraulic lines for the cylinder 42.

Each track 34 and 36 includes a series of holes 54 for mounting tool carrier 20. The tool carrier 20 supports a tool, such as an ultrasonic sizing probe P, and ensures that the probe P stays in contact with the closure seal 16. Further, the tool carrier 20 ensures that the probe P stays circumferentially centered on the closure seal 16 so that the sound path angles do not change during a scan. In FIG. 7, reference numerals 56 and 58 indicate conventional probe connections.

The movement of the tracks 34 and 36 is regulated by application of hydraulic pressure across the pistons 44 and 45. The piston stroke length is limited by the length of the chamber of cylinder 42 (or 40), and is preferably 0.920 inch. The hydraulic lines 46, 48, 50 and 52, connect the carriage assembly 22 to the remote hydraulic actuator 26 (FIGS. 8–10) which would also have a set of pistons that match the pistons 44 and 45. The remote hydraulic actuator 26 is provided to generate the necessary hydraulic pressures to actuate pistons 44 and 45 in the corresponding cylinders 40 and 42. Matching the pistons 82 and 84 in the remote actuator 26 (FIG. 8) to the pistons 44 and 45 in the carriage assembly 22 (FIGS. 5 and 6), ensures that a piston displacement in the carriage assembly 22 is identical to the piston displacement in the remote actuator 26. In this manner, a precise control over the movement of the tracks 34 and 36 can be readily obtained from a remote location.

As noted above, tracks 34 and 36 are operated individually by corresponding pistons 44 and 45. Therefore, a circumferential movement of the probe P along the closure seal 16 (arrow Y in FIG. 5) can be obtained by operating the pistons 44 and 45 of cylinders 40 and 42 simultaneously, and skewing of the probe P can be obtained by operating a single piston to thus move one of the tracks 34 and 36 (FIG. 7). In particular, operating one of the two pistons 44 and 45 in the hydraulic cylinders 40 and 42, or operating both pistons at a slightly different rate, would cause the tracks 34 and 36 to move independently of each other to thereby cause the tool carrier 20 to pivot (arrow Z is in FIG. 7). The sizing probe P may also be actuated such that it could move circumferentially in the skewed position, or be simultaneously skewed while it is being moved circumferentially.

As can be understood from the above, since the movement of the tracks 34 and 36 is limited by the corresponding piston stroke length, by mounting the tool carrier 20 at different sets of holes 54 along the length of the tracks, scanning range of the probe P over the circumference of the closure seal 16 can be varied. For example, by mounting the tool carrier 20 in the holes 54 located adjacent the top portions 60 and 62 of the tracks 34 and 36, a farther range of scan by the probe P over the circumference of the closure seal 16 may be obtained. Likewise, by mounting the tool carrier 20 in the holes 54 located adjacent the bottom portions 64 and 66 of the tracks 34 and 36, the circumferential area of the closure seal 16 lying immediately adjacent the carriage assembly 22, may be scanned.

Figure 2C:
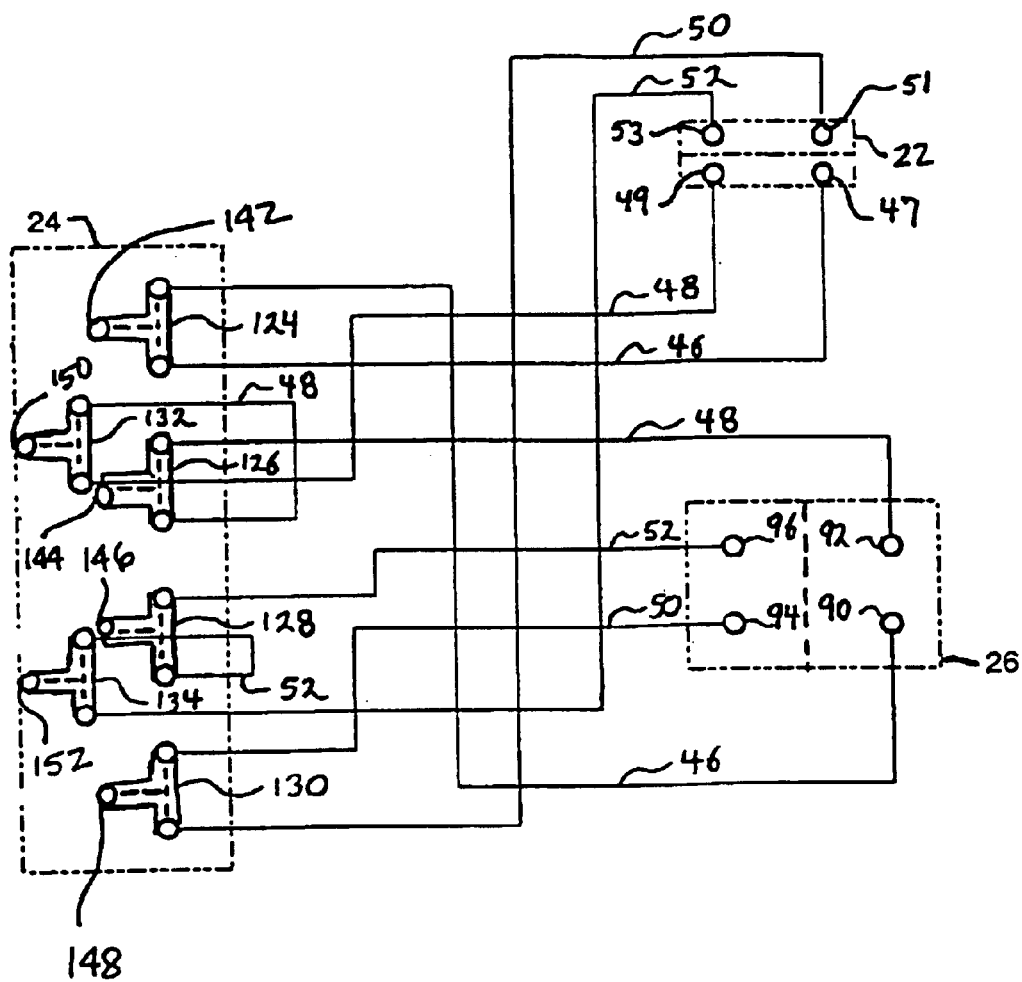
FIG. 2c is a schematic showing the hydraulic connections between the remote hydraulic actuator, the accumulator assembly and the carriage assembly.

FIGS. 2a and 2b show a top view and a side view of the remote operating system 110. The remote operating system 110 includes the accumulator assembly 24, the remote hydraulic actuator assembly 26, and a base plate 112. The base plate 112 provides support to attach the accumulator assembly 24 and the remote hydraulic assembly 26, and includes handles 114 and 116 for carrying the remote operating system 110. The carriage assembly 22 shown in FIG. 2a, is positioned remotely from the operating system 110. The carriage assembly 22 is connected to the remote operating system 110 via hydraulic lines 46, 48, 50 and 52. FIG. 2c is a schematic showing the routing of the hydraulic lines 46, 48, 50 and 52 between the carriage assembly 22, the accumulator assembly 24, and the remote hydraulic actuator assembly 26.

Figure 8:
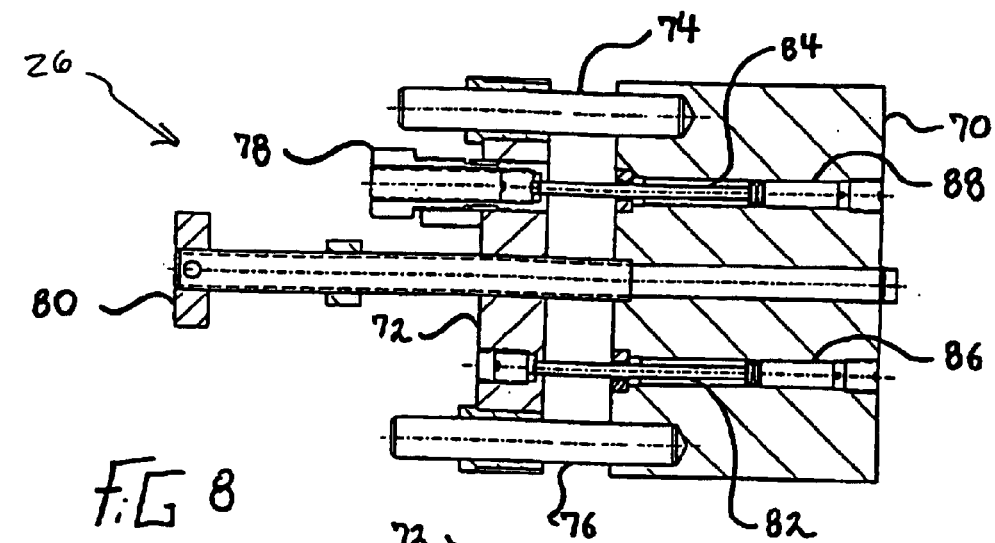
FIG. 8 is a sectional top view of the remote hydraulic actuator.
Figure 9:
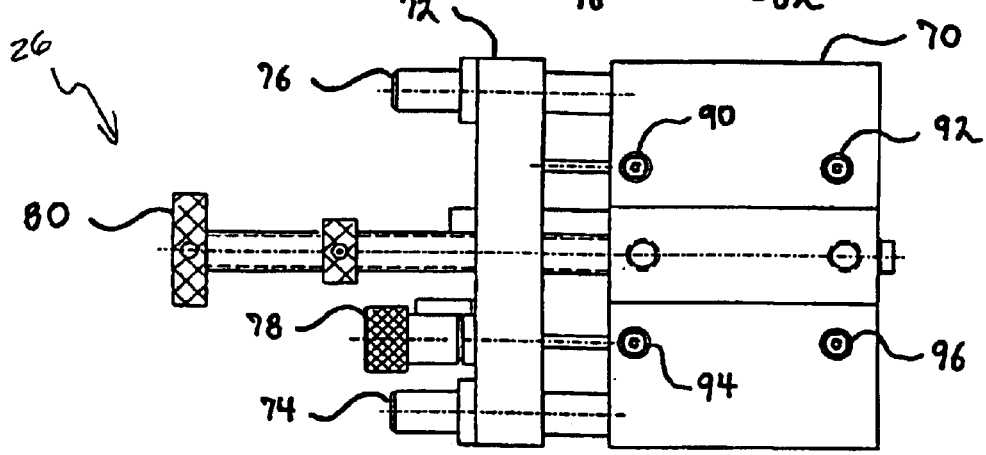
FIG. 9 is a bottom view of the remote hydraulic actuator.
Figure 10:
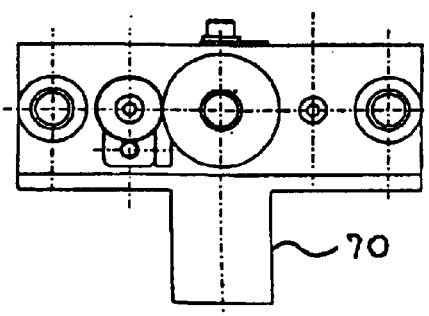
FIG. 10 is a side view of the remote hydraulic actuator.

The remote hydraulic actuator assembly 26, best shown in FIGS. 8, 9, and 10, includes an actuator body 70, a guide plate 72, guide pins 74 and 76, a skew adjuster 78, a lead screw 80, double acting pistons 82 and 84, internal cylinders 86 and 88, and four inlet/outlet ports 90, 92, 94 and 96.

As noted previously, the hydraulic actuator assembly 26 remotely actuates the double acting pistons 44 and 45 in the carriage assembly 22. The double acting pistons 82 and 84 are attached to the guide plate 72. When the lead screw 80 is turned either clockwise or counterclockwise, the guide plate 72 travels along the guide pins 74 and 76, either towards or away from the actuator body 70. This causes the double acting pistons 82 and 84 to move in the internal cylinders 86 and 88 which, in turn, causes hydraulic fluid to flow into or out of the inlet/outlet ports 90, 92, 94 and 96. This generates the necessary hydraulic pressures in the lines 46, 48, 50 and 52 to actuate the pistons 44 and 45 in the carriage assembly 22, and consequently operates the tracks 34 and 36.

The skew adjuster 78 is attached to the guide plate 72 and one of the double acting pistons 84. The skew adjuster 78 can be turned either clockwise or counterclockwise to actuate the double acting piston 84 in the internal cylinder 88 which, in turn, causes hydraulic fluid to flow into or out of the inlet/outlet ports 94 and 96. This generates the necessary hydraulic pressures in the hydraulic lines 50 and 52 to actuate the piston 45 in the carriage assembly 22, and consequently operates the track 36. Operation of a single track 36 either up or down causes the probe P to rotate in the Z direction either clockwise or counterclockwise. This is known as skewing the probe P and is necessary to obtain a clear UT signal.

As best shown in FIGS. 2a–2c, the accumulator assembly 24 includes a chambered manifold block 120, a pressure gauge 122, six three-way flow control valves 124, 126, 128, 130, 132 and 134, a fluid fill valve 136, an air control valve 138, a pulsation damper 140, and eight inlet/outlet ports 142, 144, 146, 148, 150, 152, 154 and 156.

The accumulator assembly 24 fills the entire manipulator apparatus MA with hydraulic fluid through the fluid fill valve 136. In addition, the accumulator assembly 24 bleeds air from the hydraulic lines and initializes the apparatus MA, which is necessary to synchronize the double acting pistons 82 and 84 in the remote hydraulic actuator assembly 26, with the double acting pistons 44 and 45 in the carriage assembly 22. An effective bleeding of the air from the system is preferred because even a small amount of air in the hydraulic lines would interfere with the proper operation of the tracks 34 and 36. Proper synchronization between the double acting pistons 82 and 84 in the remote hydraulic actuator assembly 26, and the double acting pistons 44 and 45 in the carriage assembly 22, is necessary to ensure that the movement of the tracks 34 and 36 corresponds with the actuation of the remote hydraulic actuator assembly 26.

The accumulator assembly 24 also provides the static pressure to the hydraulic lines 46, 48, 50 and 52 to remove sponginess from the manipulator apparatus MA. Any sponginess would interfere with the proper synchronization between the double acting pistons 82 and 84 in the remote hydraulic actuator assembly 26, and the double acting pistons 44 and 45 in the carriage assembly 22. The pressure gauge 122 is provided to monitor the static pressure in the accumulator assembly 24 and the hydraulic lines 46, 48, 50 and 52 to ensure that the correct pressure is achieved during pressurization. The manifold block 120 contains internal chambers and eight inlet/outlet ports 142, 144, 146, 148, 150, 152, 154 and 156 to enable the filling, draining, bleeding, and pressurization of the hydraulic lines 46, 48, 50 and 52. The six flow control valves 124, 126, 128, 130, 132 and 134, are used to control fluid flow to and from the manifold block 120 during the filling, draining, bleeding, and pressurization operations. The fluid fill valve 136 is provided to fill the manifold block 120 with the hydraulic fluid. Air is pumped Into the pulsation damper 140 using a pump or some other remote air source (not shown) to pressurize the accumulator assembly 24 and the hydraulic lines 46, 48, 50 and 52. The air control valve 138 is used to isolate the pulsation damper 140 from the manifold block 120.

It can be readily observed from the above that the manipulator apparatus MA of the present invention is unique in providing axial, circumferential and rotational motions for the probe P relative to the closure seal. A rotational motion is obtained by independently operable tracks 34 and 36, and a circumferential motion is obtained by changing the linear motion of the pistons 44 and 45 into radial motion about the closure seal. And, an axial motion is obtained by the delivery chain 30 that moves the manipulator apparatus MA along the longitudinal axis X of the closure seal.

As noted previously, a secondary operating actuator 27 could be provided to automate the remote actuator 26. This can be accomplished by adding a commercially available motor to operate the lead screw 80 of the remote hydraulic actuator assembly 26. A computer can be directly linked to the motor for its operation. A commercially available encoder can be used to monitor the number of rotations of the lead screw 80, and thus provide information regarding to the position of the inspection probe P. The UT signal from the inspection probe P can be directly fed into a computer in conjunction with the encoder signals. Using an available imaging software is program, the computer can be used to operate the remote hydraulic actuator assembly 26. The imaging software program analyzes the data from the encoder and the inspection probe P, and combines it to provide various scan images of flaws in the seal. The flaw image information is very useful to the UT inspector in performing an inspection of the seal. It allows the UT inspector to obtain a virtual image of the flaw in relation to the seal.

The manipulator apparatus MA of the invention utilizes hydraulics on a miniaturized scale for the precise delivery and manipulation of a miniature package in an environment with limited access. The closed hydraulic system provides the motions and forces required to manipulate a tool, such as probe P, to facilitate the characterization and sizing of ultrasonic test indications in a vessel closure seal without the removal of the closure mechanisms.

While this invention has been described as having preferred ranges, steps, materials, or designs, it is understood that it is capable of further modifications, uses and/or adaptations of the invention following in general the principle of the invention, and including such departures from the present disclosure, as those come within the known or customary practice in the art to which the invention pertains and as may be applied to the central features hereinbefore set forth, and fall within the scope of the invention and of the appended claims. It is further understood that the present invention is not limited to the claims appended hereto.

What is claimed is:

1. A method of remote delivery and manipulation of a miniature tool adjacent a work piece in a restricted space, comprising the steps of:

a) providing a manipulator apparatus, the manipulator apparatus comprising:

i) a tool carrier;

ii) a carriage assembly for manipulating the tool carrier relative to a work piece, the carriage assembly including first and second movable track members;

iii) the carriage assembly including first and second pistons for operating the first and second track members, respectively; and iv) a remote hydraulic actuator for operating the carriage assembly;

b) delivering the manipulator apparatus by a conveyor and positioning adjacent a desired area of the work piece; and c) operating the carriage assembly by actuating the remote hydraulic actuator thereby causing one or both track members move relative the work piece.

2. The method of claim 1, wherein the manipulator apparatus provided further comprises:

a) one of said first and second track members is movable independent of the other track member.

3. The method of claim 1, wherein:

a) said hydraulic actuator of the manipulator apparatus provided further comprises a plurality of actuator pistons; and b) each of said first and second track members of the carriage assembly of the manipulator apparatus provided is independently operated by a respective carriage piston.

4. The method of claim 3, wherein:

a) a the displacement of the first and second carriage pistons is substantially similar to the displacement of a corresponding actuator piston.

5. The method of claim 4, wherein the manipulator apparatus provided further comprises:

a) means for synchronizing a displacement of a carriage piston with a displacement corresponding actuator piston.

6. The method of claim 5, the manipulator apparatus provided further comprising:

a) hydraulic lines for connecting said actuator pistons with said carriage pistons; and b) means for pressurizing said hydraulic lines.

7. The method of claim 1, wherein the manipulator apparatus provided further comprises:

a) first means for moving said tool carrier in a circumferential direction of the work piece, said first means comprising a track member operably connected to said carriage assembly and movable relative thereto; and b) second means for rotating said tool carrier relative to the work piece, said second means comprising a plurality of track members operably connected to said carriage means assembly; each track member independently movable relative to said carriage assembly.

8. The method of claim 1 wherein:

a) said hydraulic actuator of the manipulator apparatus provided comprises first and second actuator pistons corresponding to said first and second pistons of the carriage assembly.

9. The method of claim 8 wherein the manipulator provided further comprises:

a) means for synchronizing a displacement of one of said first and second carriage assembly pistons with a displacement of a corresponding actuator piston.

10. The method of claim 9, wherein the manipulator apparatus provided further comprises:

a) hydraulic lines for connecting said first and second carriage assembly pistons and said first and second actuator pistons; and b) means for pressurizing said hydraulic lines.

11. The method of claim 8, wherein:

a) said first and second carriage assembly pistons and said first and second actuator pistons comprise double acting pistons.

12. The method of claim 1, wherein the manipulator apparatus provided further comprises:

a) secondary actuator for operating said hydraulic actuator.

13. The method of claim 12, wherein:

a) said secondary actuator is positioned remote from said hydraulic actuator.

14. The method of claim 13, wherein the manipulator apparatus provided further comprises:

a) means for detecting the position of the miniature tool relative to the work piece.

15. The method of claim 14, wherein:

a) the miniature tool comprises an ultrasonic testing probe; and b) said position detecting means of the manipulator apparatus provided comprises an encoder operably connected to said hydraulic actuator.

16. The method of claim 15, further comprising:

a) providing an imaging means for displaying information about the work piece.

17. The method of claim 1, wherein:

the step c) comprises moving the first and second track members substantially simultaneously to thereby cause the tool carrier to move along a single direction relative to the work piece.

18. The method of claim 1, wherein:

the step c) comprises moving only one of the first and second track members to thereby cause the tool carrier to rotate relative the work piece.

* * * * *